United States Patent
Durairaj et al.

(10) Patent No.: US 6,586,607 B1
(45) Date of Patent: Jul. 1, 2003

(54) PROCESS FOR MAKING DIGLYCIDYLETHER OF ALKOXYLATED RESORCINOL

(75) Inventors: Raj B. Durairaj, Monroeville, PA (US); Gary A. Jesionowski, Pittsburgh, PA (US)

(73) Assignee: Indspec Chemical Corporation, Pittsburgh, PA (US)

( * ) Notice: Subject to any disclaimer, the term of this patent is extended or adjusted under 35 U.S.C. 154(b) by 0 days.

(21) Appl. No.: 10/120,671

(22) Filed: Apr. 11, 2002

(51) Int. Cl.⁷ .................. C07D 301/28; C07D 303/23
(52) U.S. Cl. .................. 549/521; 549/555; 549/560
(58) Field of Search ................ 549/521, 560, 549/555

(56) References Cited

U.S. PATENT DOCUMENTS

| | | |
|---|---|---|
| 4,507,461 A | 3/1985 | Bowditch |
| 4,656,207 A | 4/1987 | Jabloner et al. |
| 4,656,208 A | 4/1987 | Chu et al. |
| 5,059,723 A | 10/1991 | Dressler |
| 5,162,547 A | 11/1992 | Roth et al. |
| 5,227,436 A | 7/1993 | Cavitt et al. |
| 5,245,048 A | 9/1993 | Rolfe et al. |
| 5,300,618 A | 4/1994 | Durairaj |
| 5,342,903 A | 8/1994 | Wolleb et al. |
| 6,303,732 B1 | 10/2001 | Durairaj |

FOREIGN PATENT DOCUMENTS

| | | |
|---|---|---|
| EP | 0 679 165 B1 | 2/1995 |
| SU | 702017 | 12/1979 |

*Primary Examiner*—Ba K. Trinh
(74) *Attorney, Agent, or Firm*—Debra Z. Anderson; Eckert Seamans Cherin & Mellott, LLC

(57) ABSTRACT

A process for the preparation of diglycidylether of alkoxylated resorcinol using novel catalysts is disclosed. In particular, it has been found that antimony, indium and tellurium halides are effective catalysts for preparation of the diglycidylether of alkoxylated resorcinol.

10 Claims, 1 Drawing Sheet

SYNTHETIC REACTION SCHEME FOR MAKING
DIGLYCIDYLETHER OF ALKOXYLATED RESORCINOL

US 6,586,607 B1

PROCESS FOR MAKING DIGLYCIDYLETHER OF ALKOXYLATED RESORCINOL

FIELD OF THE INVENTION

This invention relates to an improved process for making diglycidylether of alkoxylated resorcinol using novel catalysts. In particular, it has been discovered that halides of indium, antimony and tellurium are effective catalysts for the preparation of the epoxy resins of the present invention.

BACKGROUND INFORMATION

Epoxy resins are an important class of thermosetting polymers that exhibit properties such as high tensile strength and modulus, chemical and corrosion resistance and dimensional stability. Due to these excellent mechanical properties, epoxy resins are used in a wide range of industrial applications, including structural adhesives, coatings, and matrix resins in fiber reinforced composites.

Epoxy resins based on bisphenol A are well known and have been used extensively in various industrial applications. However, epoxy resins based on resorcinol offer additional advantages, as compared with those based on bisphenol A, as they have low viscosity and high reactivity toward various curing agents. In particular, resorcinol diglycidylether resin shows excellent cured physical and mechanical properties.

Unfortunately, resorcinol diglycidylether (RDGE) has been reported to cause skin cancer. Epoxy resins based on derivatives of resorcinol have been developed which provide similar mechanical properties as resorcinol diglycidylether but with lower toxicity. For example, U.S. Pat. No. 5,300,618 discloses epoxy resins based on 4-benzoyl resorcinol.

In the development of carbon fiber reinforced composites, epoxy resins are often cured with aromatic diamines to achieve high glass transition temperature and enhance cured resin mechanical properties. The diamine curing agents often produce high crosslink density in the cured epoxy resins, which results in low impact strength due to brittleness. To overcome this problem, toughening agents are used to improve the impact strength and fracture toughness of cured epoxy compounds. For example, U.S. Pat. Nos. 4,656,207 and 4,656,208 disclose the use of an amine terminated poly(arylether sulfone) oligomeric modifier in the development of carbon fiber reinforced composites using a resin material sold under the trade name Heloxy 69 (RDGE). European Patent 0 679 165 also discloses toughened epoxy resin systems based on substituted resorcinol-based epoxy resins and amine terminated poly(arylene ether sulfone) oligomers.

Decreasing the crosslink density in the final material can minimize the brittle character of cured epoxy resins, including resorcinol diglycidylether. This can be achieved by increasing the distance between the two epoxy groups through the introduction of linear alkyl or alkyl ether groups. The introduction of an alkylene ether group in the epoxy molecule can best be done by alkoxylating the aromatic dihydroxy compounds first, using the alkylene oxides or carbonates, before the glycidylether reaction with epichlorohydrin. Use of epoxy resins and epoxy hardeners or curing agents having such flexible akyl ether groups improves the toughness of the cured epoxy system by reducing its brittleness.

Various industrial processes and methods are known for the synthesis of bis(hydroxy ethylated) or bis(hydroxy propylated) aromatic dihydroxy compounds, using either carbonates such as ethylene or propylene carbonate, or oxides such as ethylene or propylene oxide. For example, U.S. Pat. No. 5,059,723 discloses the synthesis of bis (hydroxy ethyl) ether resorcinol from the reaction of resorcinol with ethylene carbonate. U.S. Pat. No. 6,303,732 also discloses various reaction schemes for the preparation of aromatic diols from the resorcinol and ethylene or propylene carbonate reaction. These resorcinol based aromatic diols can be used to synthesize the corresponding diglycidylethers for various high performance applications including coatings, adhesives and composites.

The synthesis of diglycidylether of alkoxylated resorcinol using an excess of epichlorohydrin has been reported. For example, Soviet Union Patent 702017 discloses the synthesis of diglycidylether of bis(hydroxy ethylated) resorcinol for high impact resistance epoxy polymers, using almost a 10-fold excess of epichlorohydrin. The method of this patent does not use a catalyst; resorcinol is reacted with ethylene chlorohydrin and sodium hydroxide in the presence of isopropyl alcohol to produce bis(hydroxy ether) resorcinol. The resulting compound is then reacted with an excess of epichlorohydrin and solid sodium hydroxide to prepare the epoxy resin.

A process in which an excess of epichlorohydrin is used may not be economical for the commercial production of epoxy resin due to the formation of sodium chloride and the added need to separate sodium chloride from the resorcinol and ethylene chlorohydrin reaction system. Additionally, the use of large quantities of epichlorohydrin and the handling of solid sodium hydroxide in the epoxy reaction are undesirable due to the hazardous nature of these materials.

To overcome the problems associated with using a large excess of epichlorohydrin, new methods and process conditions have been developed. For example, the use of hydroxy aromatics and hydroxy alkylated aromatics as starting materials permits the use of stoichiometric amounts of epichlorohydrin. However, in the case of hydroxy alkylated aromatics, special catalysts and process conditions are required to promote the reaction between hydroxy alkylated aromatics and epichlorohydrin, due to the more aliphatic nature of the hydroxy group; typically, a Lewis acid-type catalyst such as $AlCl_3$, $ZnCl_2$, $FeCl_3$, $SnCl_4$ and $BF_3$ is used.

Various patents disclose the use of these catalysts. For example, U.S. Pat. No. 4,507,461 discloses the preparation of epoxy resins from the propoxylated bisphenol A and epichlorohydrin using boron trifluoride ($BF_3$) catalyst; U.S. Pat. No. 5,162,547 discloses the preparation of epoxy resins from the aliphatic polyols such as 1,4-butanediol, trimethylol propane, sorbitol, 1,4-cyclohexane diol, etc., using tin (II) halides, preferably a tin (II) fluoride catalyst, in the presence of xylene and MIBK solvents; U.S. Pat. No. 5,227,436 also discloses the synthesis of epoxy resins from the oxyalkylated bisphenol A, prepared from bisphenol A and an alkylene oxide, and epichlorohydrin using tin (IV) chloride catalyst in the presence of methyl isobutyl ketone (MIBK) solvent; U.S. Pat. No. 5,245,048 discloses the use of perchlorate or trifluoromethane sulfonate salts of lantharium, cerium, ytterbium or yttrium as the catalysts for the epoxy resins from the aliphatic diols; and U.S. Pat. No. 5,342,903 discloses the preparation of epoxy resins from the aliphatic diols such as 1,4-butanediol, 1,4-cyclohexanediol, etc., employing lanthanide and actinide salts as the catalysts.

In spite of the above methods, there continues to be a need for novel methods and catalysts for making diglycidylether of alkoxylated resorcinol, using stoichiometric amounts of epichlorohydrin.

SUMMARY OF THE INVENTION

Accordingly, the present invention provides a method of preparation of diglycidyl ethers of the following formula:

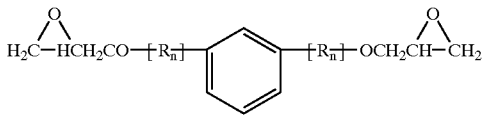

where R=an ethoxy or propoxy group and n=1 to 3 comprising:

(a) mixing a dihydroxy aromatic compound with an alkylene carbonate in the presence of a triorganophosphine catalyst using a stoichiometric excess of alkylene carbonate;

(b) reacting the mixture of step (a) at a temperature sufficient to initiate and maintain evolution of $CO_2$ for a length of time sufficient to achieve the reaction of said dihydric phenol and said alkylene carbonate to produce an aromatic diol;

(c) reacting the product of step (b) with an epihalohydrin, in the presence of a second catalyst selected from the group consisting of antimony halide, indium halide and tellurium halide, at a temperature sufficient to allow the reaction to occur;

(d) cooling the mixture of step (c) to $\leq 100°$ C.;

(e) adding a solvent to the mixture of step (d);

(f) adding a caustic to the mixture of step (e);

(g) adding water to the mixture of step (f); and (h) allowing the mixture of step (g) to settle for an amount of time sufficient to permit phase separation to occur.

Using the above method, stoichiometric amounts of the epihalohydrin can be used, avoiding the undesirable effects of an excess of this compound. The above described method provides a cost effective means of producing diglycidylether of alkoxylated resorcinol, without the need to remove excess amounts of the epihalohydrin.

It has been found that antimony, tellurium and indium halides are able to function as efficient catalysts and provide a sufficient yield of the desired end product.

It is an object of the invention, therefore, to provide a novel process for producing diglycidylether of alkoxylated resorcinol, using catalysts not previously known in the art as useful for this process.

It is an additional object of the present invention to provide a cost effective and less hazardous means of producing diglycidylether of alkoxylated resorcinol.

These and other objects of the invention will become more readily apparent from the following drawing, detailed description, examples and appended claims.

BRIEF DESCRIPTION OF THE DRAWINGS

The invention is further illustrated by the following non-limited drawings in which.

DETAILED DESCRIPTION OF THE PREFERRED EMBODIMENTS

Figure 1:
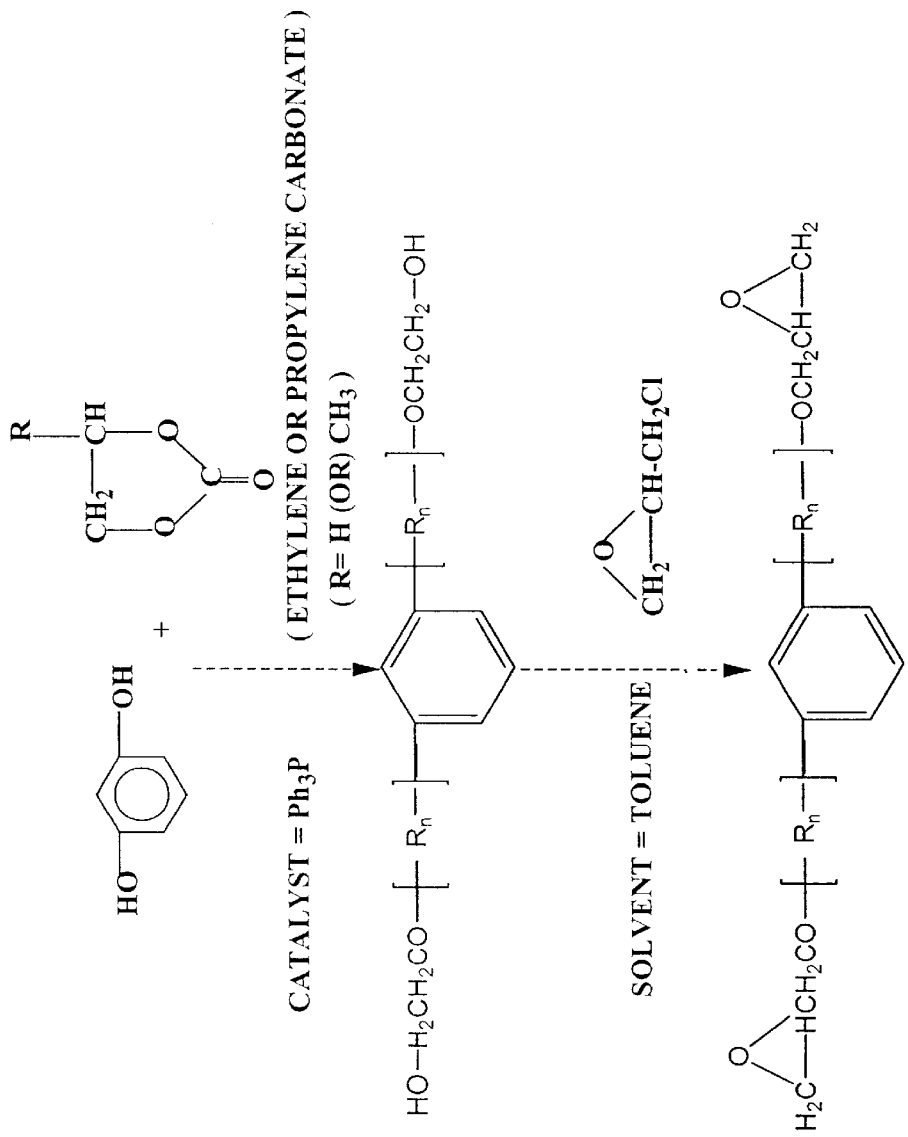
FIG. 1 is a reaction scheme for preparing diglycidylether of alkoxylated resorcinol of the present invention.

Accordingly, the present invention provides a method of preparation of diglycidyl ethers of the following formula:

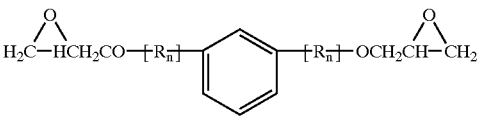

where R=an ethoxy or propoxy group and n=1 to 3 comprising:

(a) mixing a dihydroxy aromatic compound with an alkylene carbonate in the presence of a triorganophosphine catalyst using a stoichiometric excess of alkylene carbonate;

(b) reacting the mixture of step (a) at a temperature sufficient to initiate and maintain evolution of $CO_2$ for a length of time sufficient to achieve the reaction of said dihydroxyphenol and said alkylene carbonate to produce an aromatic diol;

(c) reacting the product of step (b) with an epihalohydrin, in the presence of a second catalyst selected from the group consisting of antimony halide, indium halide and tellurium halide, at a temperature sufficient to allow the reaction to occur;

(d) cooling the mixture of step (c) to $\leq 100°$ C.;

(e) adding a solvent to the mixture of step (d);

(f) adding a caustic to the mixture of step (e);

(g) adding water to the mixture of step (f); and (h) allowing the mixture of step (g) to settle for an amount of time sufficient to permit phase separation to occur.

Preparation of aromatic diols, as shown in steps (a)–(b), is well known in the art. See, for example, U.S. Pat. No. 6,303,732, expressly incorporated herein by reference, for a detailed description of methods of preparation of various aromatic diol compounds useful in the method of the present invention.

Suitable dihydroxy aromatic compounds include, for example, catechol, resorcinol, hydroquinone, bisphenols and dihydroxynaphthalenes. Preferred is resorcinol.

The alkylene carbonate compounds used according to the methods of the present invention are as described in U.S. Pat. No. 6,303,732. Preferred are ethylene carbonate and propylene carbonate.

The use of the triorganophosphine catalyst is as described in U.S. Pat. No. 6,303,732. However, use of the amounts of this catalyst described in the 6,303,732 patent appears to reduce the purity of the epoxy; it is desirable to use smaller amounts. Preferably, the amount is 0.01–10 grams triorganophosphine catalyst per mole of aromatic diol, more preferably 0.01–2 grams per mole, most preferably 0.01–0.5 grams per mole. The details of the reaction are as otherwise described in the 6,303,732 patent. Alternatively, various aromatic diol mixtures are commercially available, such as the ones sold under the trade names HER HP and HER TG-210 (high purity and technical grade, respectively, bis (hydroxy ethyl) ether of resorcinol), by Indspec Chemical Corporation of Pittsburgh, Pennsylvania.

The aromatic diol produced in step (b) is mixed with the epihalohydrin, in the presence of a second catalyst selected from the group consisting of antimony halide, indium halide and tellurium halide. Any epihalohydrin can be used; preferred are epichlorohydrin and epibromohydrin. The aromatic diol and epihalohydrin are mixed in a ratio of about 1 mole aromatic diol to 2–4 moles epihalohydrin; preferred is about one mole aromatic diol to about 2–2.1 moles epihalohydrin.

The concentration of the second catalyst is based on the amount of the aromatic diol and typically ranges from about 1 to 10 wt. %; preferably, the catalyst concentration is about 2 to 3% based on the weight of the aromatic diol. Any halide can be used; preferred salts are fluoride and chloride.

The reaction of the aromatic diol and epihalohydrin is carried out at reflux temperature, which is typically about 100° to 150° C., more preferably about 115° to 140° C., over a period of about 2 to 20 hours. The reaction time will vary depending on the temperature used; a preferred reaction time is about 5 to 9 hours. The epihalohydrin is added slowly to control the rate of the exothermic reaction.

After the reaction of the aromatic diol and the epihalohydrin is complete, the reaction mixture is allowed to cool to less than about 100° C., after which a solvent is added. Any inert organic solvent can be used, including standard halogenated hydrocarbon solvents, ketosolvents or other solvents which do not interfere with the reaction. Preferred is toluene.

Following the addition of a solvent, a caustic such as sodium hydroxide is added to dehydrohalogenate the chlorohydrin intermediate and neutralize the formation of acid. Addition of the caustic is done slowly over a period of time, and is usually done over a period of about 1 to 10 hours, more preferably, 1 to 1½ hours. A 10% to 70% caustic solution can be used; preferably, a 50% caustic solution is used. After the addition of the caustic, the mixture is allowed time to react and the reaction is run to completion; typically this will take between about 1 and 10 hours, more preferably between about 1 and 2 hours.

Water is then added to the reaction mixture to dissolve the slurry; the amount used will vary depending on the salt content. After addition of the water, the reaction mixture is allowed to settle, thus permitting draining of the water. The reaction mixture must sit long enough for a phase separation to occur.

EXAMPLES

The following examples are intended to illustrate the invention, and should not be construed as limiting the invention in any way.

Example 1

Synthesis of Diglycidyl Ether of Alkoxylated Resorcinol Using Antimony (III) Fluoride Catalyst HER HP (39.64 grams; 0.2 mole) and antimony (III) fluoride (1.19 grams) were placed in a 250 ml round-bottom flask with a mechanical stirrer, thermometer, reflux condenser, and an addition funnel. The contents were heated to 130° C. Epichlorohydrin (38.8 grams; 0.42 mole) was slowly added to the solution from the addition funnel for 0.5 hour. The solution was further reacted at temperature for another 5.5 hours. The solution was then cooled to room temperature. Toluene (60 grams) was added and the temperature raised to 80° C. A 50% (w/w) sodium hydroxide solution (35.2 grams; 0.44 mole NaOH) was slowly added over a 1-hour period and then the contents were held at 80° C. for an additional 1.5 hour. Distilled water (80 grams) was added to the solution and the temperature returned to 80° C. The aqueous phase was drained and discarded. The organic phase was washed two more times with distilled water. The toluene was removed on a rotary evaporator at 95–100° C. and 27–28" Hg vacuum, leaving 58.1 grams of epoxide with 7.1 wt. % oxirane oxygen, EEW=224, and 5.5 wt. % total chlorine. NMR analysis indicated an average of 1.54 glycidyl ether groups per molecule.

Example 2

Synthesis of Diglycidyl Ether of Alkoxylated Resorcinol Using Antimony (III) Fluoride Catalyst HER HP (396.4 grams; 2.0 moles) and antimony (III) fluoride (11.9 grams) were placed in a 3 liter round-bottom flask with a mechanical stirrer, thermometer, reflux condenser, and an addition funnel. The contents were heated to 130° C. Epichlorohydrin (388.5 grams; 4.2 moles) was slowly added to the solution from the addition funnel for 1 hour. The solution was further reacted at temperature for another 5.5 hours. The solution was then cooled to room temperature. Toluene (600 grams) was added and the temperature raised to 90° C. A 50%(w/w) sodium hydroxide solution (352.0 grams; 4.4 moles NaOH) was slowly added over a 1-hour period and then the contents were held at 90° C. for an additional 2 hours. Distilled water (700 grams) was added to the solution and the temperature returned to 80° C. The aqueous phase was drained and discarded. The organic phase was washed two more times with distilled water. The toluene was removed on a rotary evaporator at 95–100° C. and 27–28" Hg vacuum, leaving 595.3 grams of epoxide with 6.7 wt. % oxirane oxygen, EEW=240, and 5.9 wt. % total chlorine. NMR analysis indicated an average of 1.51 glycidyl ether groups per molecule.

Example 3

Synthesis of Diglycidyl Ether of Alkoxylated Resorcinol From Technical-Grade HER (TG-210) Using Antimony (III) Fluoride Catalyst HER TG-210 (40.5 grams; 0.2 mole; hydroxyl number= 554) and antimony (III) fluoride (1.0 grams) were placed in a 250 ml round-bottom flask with a mechanical stirrer, thermometer, reflux condenser, and an addition funnel. The contents were heated to 120° C. Epichlorohydrin (37.9 grams; 0.41 mole) was slowly added to the solution from the addition funnel for 1 hour. The solution was further reacted at temperature for another 9 hours. The solution was then cooled to room temperature. Toluene (60 grams) was added and the temperature raised to 80° C. A 50% (w/w) sodium hydroxide solution (33.6 grams; 0.42 mole NaOH) was slowly added over a 1-hour period and then the contents were held at 80° C. for an additional 1.5 hour. Distilled water (70 grams) was added to the solution and the temperature returned to 80° C. The aqueous phase was drained and discarded. The organic phase was washed two more times with distilled water. The toluene was removed on a rotary evaporator at 95–100° C. and 27–28" Hg vacuum, leaving 61.5 grams of epoxide with 6.9 wt. % oxirane oxygen, EEW=231, and 5.4 wt. % total chlorine. NMR analysis indicated an average of 1.5 glycidyl ether groups per molecule.

Example 4

Synthesis of Diglycidyl Ether of Alkoxylated Resorcinol Using Tellurium Tetrachloride Catalyst HER HP (59.4 grams; 0.3 mole) and tellurium tetrachloride (3.2 grams) were placed in a 500 ml round-bottom flask with a mechanical stirrer, thermometer, reflux condenser, and an addition funnel. The contents were heated to 130° C. Epichlorohydrin (56.9 grams; 0.615 mole) was slowly added to the solution from the addition funnel for 0.5 hour. The solution was further reacted at temperature for another 5 hours. The solution was then cooled to room temperature. Toluene (90 grams) was added and the temperature raised to 62° C. A 50% (w/w) sodium hydroxide solution (49.2 grams; 0.615 mole NaOH) was slowly added over a 1-hour period and then the contents were held at 62° C. for an additional 1 hour. Distilled water (100 grams) was added to the solution and the temperature returned to 60° C. The aqueous phase was drained and discarded. The organic phase was washed two more times with distilled water. The toluene was removed on a rotary evaporator at 85° C. and 27–28" Hg vacuum, leaving 15.1 grams of epoxide with 6.2 wt. % oxirane oxygen, EEW=257, and 1.0 wt. % total chlorine. NMR analysis indicated an average of 1.04 glycidyl ether groups per molecule.

Example 5

Synthesis of Diglycidyl Ether of Alkoxylated Resorcinol Using Indium (III) Chloride Catalyst HER HP (59.4 grams; 0.3 mole) and indium (III) chloride (1.78 grams) were placed in a 500 ml round-bottom flask with a mechanical stirrer, thermometer, reflux condenser, and an addition funnel. The contents were heated to 130° C. Epichlorohydrin (56.9 grams; 0.615 mole) was slowly added to the solution from the addition funnel for 1 hour. The solution was further reacted at temperature for another 5 hours. The solution was then cooled to room temperature. Toluene (90 grams) was added and the temperature raised to 62° C. A 50% (w/w) sodium hydroxide solution (49.2 grams; 0.615 mole NaOH) was slowly added over a 1-hour period and then the contents were held at 62° C. for an additional 1 hour. Distilled water (100 grams) was added to the solution and the temperature returned to 60° C. The aqueous phase was drained and discarded. The organic phase was washed two more times with distilled water. The toluene was removed on a rotary evaporator at 95–100° C. and 27–28" Hg vacuum, leaving 89.0 grams of epoxide with 7.4 wt. % oxirane oxygen, EEW=215, and 3.8 wt. % total chlorine.

Example 6

Synthesis of Diglycidyl Ether of Alkoxylated Resorcinol Using Boron Trifluoride-Phenol Complex Catalyst For comparative purposes, $BF_3$ was used as a catalyst. HER HP (59.4 grams; 0.3 mole) and boron trifluoride-phenol complex (1.9 grams) were placed in a 500 ml round-bottom flask with a mechanical stirrer, thermometer, reflux condenser, and an addition funnel. The contents were heated to 130° C. Epichlorohydrin (56.9 grams; 0.615 mole) was slowly added to the solution from the addition funnel for 1 hour. The solution was further reacted at temperature for another 5 hours. The solution was then cooled to room temperature. Toluene (90 grams) was added and the temperature raised to 62° C. A 50% (w/w) sodium hydroxide solution (49.2 grams; 0.615 mole NaOH) was slowly added over a 1 hour period and then the contents were held at 62° C. for an additional 1 hour. Distilled water (100 grams) was added to the solution and the temperature returned to 60° C. The aqueous phase was washed two more times with distilled water. The toluene was removed on a rotary evaporator at 95–100° C. and 27–28" Hg vacuum, leaving 92.3 grams of epoxide with 7.0 wt. % oxirane oxygen, EEW=228, and 5.1 wt. % total chlorine. NMR analysis indicated an average of 1.54 glycidyl ether groups per molecule.

Example 7

Synthesis of Diglycidyl Ether of Alkoxylated Resorcinol Using Antimony (III) Fluoride Catalyst (2.05 mole EPI/mole HER HP)

HER HP (59.4 grams; 0.3 mole) and antimony (III) fluoride (1.78 grams) were placed in a 500 ml round-bottom flask with a mechanical stirrer, thermometer, reflux condenser, and an addition funnel. The contents were heated to 130° C. Epichlorohydrin (56.9 grams; 0.615 mole) was slowly added to the solution from the addition funnel for 1 hour. The solution was further reacted at temperature for another 5 hours. The solution was then cooled to room temperature. Toluene (90 grams) was added and the temperature raised to 62° C. A 50% (w/w) sodium hydroxide solution (49.2 grams; 0.615 mole NaOH) was slowly added over a 1-hour period and then the contents were held at 62° C. for an additional 1 hour. Distilled water (100 grams) was added to the solution and the temperature returned to 60° C. The aqueous phase was drained and discarded. The organic phase was washed two more times with distilled water. The toluene was removed on a rotary evaporator at 80° C. and 27–28" Hg vacuum, leaving 90.8 grams of epoxide with 6.6 wt. % oxirane oxygen, EEW=242, and 6.3 wt. % total chlorine. NMR analysis indicated an average of 1.52 glycidyl ether groups per molecule.

Examples 8–9

Reaction of HER HP and Epichlorohydrin Effect of Excess Epichlorohydrin (Antimony (III) Fluoride Catalyst)

In the following examples, HER HP (39.64 grams; 0.2 mole) and antimony (III) fluoride (0.79 grams) were placed in a 250 ml round-bottom flask with a mechanical stirrer, thermometer, reflux condenser, and an addition funnel. The contents were heated to the desired temperature and epichlorohydrin (55.5 grams; 0.6 mole) was slowly added to the solution. The solution was further reacted at temperature for 5 hours. Samples were taken for GC analysis of unreacted HER and epichlorohydrin. The excess epichlorohydrin could be distilled off and these solutions could then be further reacted as described in Example 1 to produce the diglycidyl ether of alkoxylated resorcinol.

| EXAMPLE # | Reaction Temp (° C.) | HER HP (weight %) | Epichlorohydrin (wt %) |
| --- | --- | --- | --- |
| 8 | 110 | 12 | 33 |
| 9 | 130 | 4.4 | 19 |

Example 10

Synthesis of Diglycidyl Ether of Propoxylated Resorcinol Using Antimony (III) Fluoride Catalyst Hydroxy propyl ether of resorcinol (46.4 grams; 0.2 mole; hydroxyl number=484) and antimony (III) fluoride (1.4 grams) were placed in a 250 ml round-bottom flask with a mechanical stirrer, thermometer, reflux condenser, and an addition funnel. The contents were heated to 130° C. Epichlorohydrin (37.9 grams; 0.41 mole) was slowly added to the solution from the addition funnel for 1 hour. The solution was further reacted at temperature for another 6 hours. The solution was then cooled to room temperature. Toluene (60 grams) was added and the temperature raised to 80° C. A 50% (w/w) sodium hydroxide solution (33.6 grams; 0.42 mole NaOH) was slowly added over a 1-hour period and then the contents were held at 80° C. for an additional 1.5 hour. Distilled water (80 grams) was added to the solution and the temperature returned to 80° C. The aqueous phase was drained and discarded. The organic phase was washed two more times with distilled water. The toluene was removed on a rotary evaporator at 95–100° C. and 27–28" Hg vacuum, leaving 69.6 grams of epoxide with 5.7 wt. % oxirane oxygen, EEW=283, and 5.8 wt. % total chlorine. NMR indicated an average of 1.27 glycidyl ether groups per molecule.

Example 11

Synthesis of Diglycidyl Ether of Hydroquinone bis (2-Hydroxyethyl) Ether Using Antimony (III) Fluoride Catalyst Hydroquinone bis(2-hydroxyethyl) ether (39.3 grams; 0.2 mole; hydroxyl number=571) and antimony (III) fluoride (0.98 grams) were placed in a 250 ml round-bottom flask with a mechanical stirrer, thermometer, reflux condenser, and an addition funnel. The contents were heated to 130° C. Epichlorohydrin (37.9 grams; 0.41 mole) was slowly added to the solution from the addition funnel for 1 hour. The solution was further reacted at temperature for another 6 hours. The solution was then cooled to room temperature. Toluene (60 grams) was added and the temperature raised to 80° C. A 50% (w/w) sodium hydroxide solution (33.6 grams; 0.42 mole NaOH) was slowly added over a 1-hour period and then the contents were held at 80° C. for an additional 1.5 hour. Distilled water (70 grams) was added to the solution and the temperature returned to 80° C. The aqueous phase was drained and discarded. The organic phase was washed two more times with distilled water. The toluene was removed on a rotary evaporator at 95–100° C. and 27–28" Hg vacuum, leaving 61.1 grams of epoxide with 6.9 wt. % oxirane oxygen, EEW=230, and 5.8 wt. % total chlorine. NMR indicated an average of 1.51 glycidyl ether groups per molecule.

Example 12

Synthesis of Diglycidyl Ether of Alkoxylated Resorcinol From Resorcinol and Ethylene Carbonate Using Tin (II) Fluoride Catalyst Ethylene carbonate (74.0 grams; 0.84 mole) was placed in a 500 ml round-bottom flask with a mechanical stirrer, thermometer, reflux condenser, addition funnel, and a gas inlet tube. It was heated to 60° C. and a nitrogen sweep was turned on in the headspace of the flask. Resorcinol (44.0 grams; 0.4 mole) and triphenylphosphine (0.06 grams) were added to the flask and the contents were heated to 138° C. The nitrogen flow was turned off and the reaction proceeded for 17.4 hours while the temperature was gradually increased to 169° C. Upon completion, the nitrogen was turned back on and the reactor contents cooled to 120° C. Tin (II) fluoride (2.0 grams) was added to the flask. Epichlorohydrin (75.9 grams; 0.82 moles) was slowly added to the solution from the addition funnel for 1 hour. The solution was further reacted at temperature for another 8 hours. The solution was then cooled to room temperature. Toluene (120 grams) was added and the temperature raised to 80° C. A 50% (w/w) sodium hydroxide solution (67.2 grams; 0.84 moles NaOH) was slowly added over a 1-hour period and then the contents were held at 80° C. for an additional 1.5 hour. Distilled water (160 grams) was added to the solution and the temperature returned to 80° C. The aqueous phase was drained and discarded. The organic phase was washed two more times with distilled water. The toluene was removed on a rotary evaporator at 95–100° C. and 27–28" Hg vacuum, leaving 110.1 grams of epoxide with 7.0 wt. % oxirane oxygen, EEW=230, and 3.5 wt. % total chlorine. NMR analysis indicated an average of 1.43 glycidyl ether groups per molecule.

Whereas particular embodiments of this invention have been described above for purposes of illustration, it will be evident to those skilled in the art that numerous variations of the details of the present invention may be made without departing form the invention as described in the appended claims.

What is claimed is:

1. A method of preparing of diglycidyl ethers of the following formula:

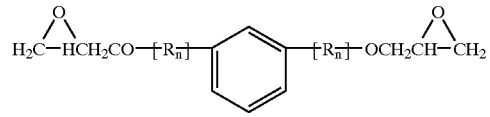

where R=an ethoxy or propoxy group and n=1 to 3 comprising:

(a) mixing a dihydroxy aromatic compound with an alkylene carbonate in the presence of a triorganophosphine catalyst using a stoichiometric excess of alkylene carbonate;

(b) reacting the mixture of step (a) at a temperature sufficient to initiate and maintain evolution of $CO_2$ for a length of time sufficient to achieve the reaction of said dihydric phenol and said alkylene carbonate to produce an aromatic diol;

(c) reacting the product of step (b) with an epihalohydrin, in the presence of a second catalyst selected from the group consisting of antimony trihalide, indium halide and tellurium halide, at a temperature sufficient to allow the reaction to occur;

(d) cooling the mixture of step (c) to $\leq 100°$ C.;

(e) adding a solvent to the mixture of step (d);

(f) adding a caustic to the mixture of step (e);

(g) adding water to the mixture of step (f); and (h) allowing the mixture of step (g) to settle for an amount of time sufficient to permit phase separation to occur.

2. The method of claim 1, wherein the molar ratio of said aromatic diol to said epihaloydrin is about 1 to 2–4.

3. The method of claim 1, wherein step (c) is carried out at a reaction temperature of about 100°–150° C., over a period of about 2 to 20 hours.

4. The method of claim 1, wherein said second catalyst is present in an amount of about 1–10 wt. %, based on the weight of the aromatic diol.

5. The method of claim 1, wherein said triorganophosphine catalyst is triphenylphosphine.

6. The method of claim 1, wherein said triorganophosphine catalyst is present in an amount of about 0.01 to 10 grams per mole of aromatic diol.

7. The method of claim 1, wherein said dihydroxy aromatic compound is resorcinol.

8. The method of claim 1, wherein said akylene carbonate is ethylene carbonate.

9. The method of claim 1, wherein said alkylene carbonate is propylene carbonate.

10. The method of claim 1, wherein said epihalohydrin is epichlorohydrin.

* * * * *